United States Patent [19]

Kuroda et al.

[11] Patent Number: 5,854,384

[45] Date of Patent: *Dec. 29, 1998

[54] PROCESS FOR PREPARING POLY-α-AMINO ACID PARTICLES

[75] Inventors: Kyoko Kuroda; Masayuki Hattori; Yoshitaka Yamakawa, all of Tsuchiura; Kenya Makino, Tokushima; Toshio Hayashi, Sakai, all of Japan

[73] Assignee: SR Corporation, Tokyo, Japan

[*] Notice: The term of this patent shall not extend beyond the expiration date of Pat. No. 5,852,109.

[21] Appl. No.: 719,544

[22] Filed: Sep. 25, 1996

[30] Foreign Application Priority Data

Sep. 26, 1995 [JP] Japan .................................... 7-247887
Apr. 24, 1996 [JP] Japan .................................... 8-102128

[51] Int. Cl.$^6$ .................................................. C08G 69/00
[52] U.S. Cl. .......................... 528/355; 528/354; 528/357; 528/403; 528/408; 528/409
[58] Field of Search ..................................... 526/260, 258, 526/217, 220; 424/489, 497; 528/408, 403, 409, 355

[56] References Cited

U.S. PATENT DOCUMENTS 4,525,495  6/1985  Dorman .................... 523/205

OTHER PUBLICATIONS

JP 4041526 –Feb. 12, 1992 –Derwent Abstract.
JP 3095223 –Apr. 19, 1991 –Derwent Abstract.
JP 93013168 –Feb. 19, 1993 –Derwent Abstract.
JP 51087597 –Jul. 31, 1976 –Derwent Abstract.

*Primary Examiner*—Fred Zitomer
*Attorney, Agent, or Firm*—Oblon, Spivak, McClelland, Maier & Neustadt, P.C.

[57] ABSTRACT

A process for preparing poly-α-amino acid particles comprising polymerizing an α-amino acid-N-carboxy anhydride using a polymerization initiator in an organic solvent in which both the solubility of the α-amino acid-N-carboxy anhydride and the solubility of the produced poly-α-amino acid are 0.1 g/100 ml or less at 25° C. Polyamino acid particles having a high molecular weight and a small bulk specific gravity can be manufactured very easily without requiring specific procedures. The polyamino acid particles can be used as a coating material for papers, resins, rubbers, and fibers; particles for cosmetics; particles for diagnostic drugs; fillers for chromatography; and an encapsulating material for drugs, fertilizers, and perfumes.

7 Claims, No Drawings

PROCESS FOR PREPARING POLY-α-AMINO ACID PARTICLES

BACKGROUND OF THE INVENTION

1. Field of the Invention

The present invention relates to a process for preparing poly-α-amino acid particles by the polymerization of an α-amino acid-N-carboxy anhydride (hereinafter abbreviated to "amino acid-NCA") using a polymerization initiator in an organic solvent, and, more particularly to a process for preparing poly-α-amino acid particles by heterogeneously polymerizing an amino acid-NCA using an organic solvent in which both the solubility of the amino acid-NCA and the solubility of the produced poly-α-amino acid are 0.1 g/100 ml or less.

2. Description of the Background Art

Because polyamino acid is decomposed by microorganisms and possesses superior characteristics such as high permeability to oxygen and water, polyamino acid is a suitable polymer for a natural environment in spite of its solid properties. Because of these superior characteristics, polyamino acid is particularly useful as a coating material for papers, resins, rubbers, and fibers; particles for cosmetics; particles for diagnostic drugs; as fillers for chromatography; and an encapsulating material for drugs, fertilizers, and perfumes. Uses for polyamino acid are expected to develop in the future.

A conventional process for the manufacture of polyamino acid comprises dissolving an amino acid-NCA in an anhydrous organic solvent and subjecting the solution to homogeneous solution polymerization using a polymerization initiator such as an amine compound. If a polyamino acid in powdery form can be directly obtained, this can be expected to be a new material for cosmetic, drugs, and agricultural chemicals.

However, the conventional process using the homogeneous solution polymerization of amino acid-NCA cannot directly produce a polyamino acid powder.

One of the conventional processes for manufacturing polyamino acid particles comprises preparing a polymer solution by dissolving solid polyamino acid in an organic solvent or by homogeneously polymerizing amino acid NCA in an organic solvent, adding water and an emulsifying agent to emulsify the polymer solution, and removing the organic solvent (hereinafter called a re-emulsification process; Japanese Patent Application Laid-open (kokai) 13168/1993).

The other processes for manufacturing polyamino acid particles include: a process for polymerizing amino acid-NCA using an organic solvent which can dissolve the amino acid-NCA, but cannot dissolve polyamino acid ("precipitation polymerization process"; e.g. Japanese Patent Application Laid-open (kokai) No. 87597/1976); a process for polymerizing amino acid-NCA in the solid phase without using a solvent to produce a polyamino acid powder ("solid phase polymerization process"; e.g. Japanese Patent Application Laid-open (kikai) No. 95223/1995); and a process comprising dissolving amino acid-NCA in an organic solvent which can dissolve the amino acid-NCA, but cannot dissolve polyamino acid, dispersing the solution in an organic solvent which cannot dissolve this solution, and polymerizing the amino acid-NCA (non-homogeneous polymerization process; Japanese Patent Application Laid-open (kokai) No. 41526/1992).

Using the re-emulsification process, an emulsion or particles of target polyamino acid can be manufactured only by a complicated process in steps which comprise (i) preparing a polymer solution, (ii) emulsifying the polymer solution in water, and (iii) removing the organic solvent.

The process for manufacturing polyamino acid particles by precipitation polymerization involves problems such as production of particles with non-uniform particle sizes, and difficulty in controlling the particle size. A drawback of the solid phase polymerization process is the difficulty in uniformly supplying the polymerization initiator to the solid phase, which makes it difficult to control the molecular weight and to produce particles with a uniform particle size. The non-homogeneous polymerization process requires use of two organic solvents which must be selected according to the type of amino acid-NCA used. This makes the process complicated and limits the area in which this process can be applied.

SUMMARY OF THE INVENTION

An object of the present invention is therefore to overcome the problems in the conventional processes and to provide an industrially applicable process for directly manufacturing polyamino acid powder.

This object can be achieved in the present invention by a process for preparing poly-α-amino acid particles comprising polymerizing an α-amino acid-N-carboxy anhydride using a polymerization initiator in an organic solvent in which both the solubility of α-amino acid-N-carboxy anhydride and the solubility of the produced poly-α-amino acid are 0.1 g/100 ml or less at 25° C.

Other objects, features and advantages of the invention will hereinafter become more readily apparent from the following description.

DETAILED DESCRIPTION OF THE INVENTION AND PREFERRED EMBODIMENTS

In the process of the present invention, the amino acid-NCA is suspended in an organic solvent in which both the solubility of the amino acid-NCA and the solubility of the polymer of the amino acid-NCA (hereinafter simply called polyamino acid) are 0.1 g/100 ml or less at 25° C. (such an organic solvent is hereinafter called a "specific organic solvent"), and the amino acid-NCA is polymerized using a polymerization initiator which is dissolved in the specific organic solvent.

The polymerization initiator dissolved in the specific organic solvent acts uniformly on suspended particles of amino acid-NCA and can initiate the polymerization reaction. As a result, homogeneous particles of polyamino acid can be produced. Because the poly-α-amino acid powder produced is obtained as a suspension, the polymer particles can be easily separated from the specific organic solvent by filtration or the like. In addition, because additives such as an emulsifying agent are not required, polyamino acid powder with a high purity can be easily obtained.

The process of the present invention will be described in more detail below.

The amino acid-NCA which is used in the present invention may be any amino acid-NCA derived from any α-amino acid. Examples of such an α-amino acid include, (a) neutral amino acid, such as glycine, alanine, valine, norvaline, leucine, isoleucine, norleucine, phenylalanine, methionine, and proline; (b) acidic amino acid-ω-esters, such as glutamic acid-γ-ester, and aspartic acid-β-ester (here alcohol residues forming the esters include alkyl groups, cycloalkyl groups, and aryl groups having 1–20, preferably 1–15, carbon atoms, such as a methyl group, ethyl group, butyl group, cyclohexyl group, phenyl group, and benzyl group); (c) N-acyl basic amino acid such as N-carbobenzoxylysine, N-carbobenzoxyornithine, and N-acetyllysine (here, as the acyl group, a group containing 1–20, preferably 1–15, carbon atoms is appropriate); and (d) esters of a hydroxyl group-containing α-amino acid, such as serine, threonine, and tyrosine (here, carboxylic acid residues which form esters include groups containing 1–20, preferably 1–15, carbon atoms, such as a methyl group, ethyl group, butyl group, octyl group, cyclohexyl group, phenyl group, benzyl group, and naphthalene methyl group).

Among these α-amino acids, those having a functional group such as a carboxyl group, hydroxyl group, thiol group, amino group, guanidyl group in a side chain, must be converted into an amino acid-NCA after these functional groups have been protected using a suitable protective group.

Preferred amino acid-NCAs among these are NCAs of an ester of glutamic acid or aspartic acid, NCAs of an N-acyl compound of lysine, and NCAs of glycine or alanine.

These amino acid-NCAs may be an optically active isomer, a racemate, or a mixture of amino acid-NCAs. Furthermore, crystals of these amino acids may be previously pulverized or may be made into a fine powder.

Any organic solvent of which both the solubility of polyamino acid-NCA and the solubility of the produced polyamino acid is 0.1 g/100 ml or less, and preferably 0.05 g/100 ml or less, at 25° C., and which does not interfere with the polymerization of the amino acid-NCA, can be used as the specific organic solvent in the present invention without any specific limitations.

The following solvents can be given as examples of the specific organic solvent used in the present invention: aliphatic hydrocarbons having 5–20, preferably 5–10, carbon atoms, such as n-pentane, n-hexane, n-heptane, n-octane, iso-octane, and cyclohexane; aromatic hydrocarbons having 6–9, preferably 6–8, carbon atoms, such as benzene, toluene, and xylene; ethers having 4–20, preferably 4–16, carbon atoms, such as diethyl ether, diisopropyl ether, dibutyl ether, dihexyl ether, dioctyl ether, and ethoxy benzene.

It is desirable that these specific organic solvents be dry, with a water content of 2 wt % or less, preferably 1 wt % or less.

These specific organic solvents may be used either individually or as a mixture of two or more.

Preferred combinations of amino acid-NCA and an organic solvent used in the process of the present invention are as follows:

Hydrocarbons (e.g. cyclohexane) or ethers (e.g. diethyl ether, diisopropyl ether) are preferably used as the organic solvent for amino acid-NCAs such as glutamic acid-γ-methyl ester-NCA (MLG-NCA), glutamic acid-γ-ethyl ester-NCA (ELG-NCA), glutamic acid-γ-benzyl ester-NCA (BLG-NCA), or aspartic acid-β-ester-NCA; and ethers (e.g. diisopropyl ether) are preferred as the organic solvent for amino acid-NCAs such as alanine-NCA, leucine-NCA, or N-carboxybenzoxylysine-NCA.

Any polymerization initiators commonly used in the polymerization of amino acid-NCA can be used in the present invention. Amine compounds or metal alcoholates are given as examples of preferred polymerization initiators. Because amine compounds are abundantly soluble in the above-mentioned specific organic solvents, there are no problems with solubility. However, because many metal alcoholates have poor solubility in specific organic solvents, those having a solubility of at least 0.01 g/100 ml, preferably 0.05 g/100 ml, at 25° C. must be selected.

Given as specific examples of polymerization initiators are primary amines, such as methyl amine, ethyl amine, isopropylamine, and butyl amine; secondary amines, such as dimethylamine, diethylamine, and dibutylamine; ternary amines, such as trimethylamine, triethylamine, tributylamine; alcohol amines, such as ethanolamine, diethanolamine, triethanolamine, and N,N-dimethyl ethanolamine; amino compounds, including polyamines such as ethylenediamine, hexamethylenediamine, N,N-dimethyl-1, 3-propanediamine, triethylenediamine; and metal alcoholates made from a metal such as lithium, sodium, or potassium and an alcohol such as methyl alcohol, ethyl alcohol, propyl alcohol, butyl alcohol, hexyl alcohol, 2-ethylhexyl alcohol, or benzyl alcohol.

The proportion of the amino acid-NCA for the specific organic solvent used in the present invention is usually 1 to 50 wt %, preferably 5 to 30 wt %.

The polymerization initiator is usually used in the proportion of 0.0002 to 0.5 mol, preferably 0.001 to 0.2 mol, for one mol of the amino acid-NCA.

Polymerization of amino acid-NCA is carried out by mechanically stirring the reaction mixture in a reactor, preferably at 10 to 3000 rpm, and more preferably at 20 to 3000 rpm. There are no specific limitations to the polymerization pressure. The polymerization temperature is usually −30° to 100° C., and preferably 0° to 90° C.

Optimum conditions are selected from among the above-described conditions depending on the type of amino acid-NCA, the specific organic solvent, and the polymerization initiator used in the reaction, and also according to the molecular weight of the target polyamino acid. Preferably, a simple experiment is carried out to select optimum conditions for each case.

A method for separating polyamino acid particles by filtration and drying the particles, a method for separating polyamino acid particles by centrifugation and drying the particles, and a method for freeze-drying (when cyclohexane is used as the specific organic solvent) can be used for separating polyamino acid particles from the reaction medium.

The molecular weight of the polyamino acid obtained by the process of the present invention is preferably 10,000 to 500,000.

For the determination of the molecular weight of the polyamino acid, the limited viscosity [η] of a sample with a known absolute molecular weight M is measured, and a coefficient K and a coefficient a are determined from the following equation.

$$[\eta] = K \cdot M^a$$

A viscosity formula (coefficient) of P. Doty, J. H. Bradbury, and A. M. Holtzer, J. Am. Chem. Soc., 78, 947 (1956) was used as the measurement conditions of general polymers in the present invention.

The average particle diameter of the polyamino acid particles is in the range of 0.1 to 100 μm and the fluctuating coefficient (CV value) is usually in the range of 2 to 80%.

The polyamino acid particles of the present invention are porous with a bulk specific gravity of 0.35 g/ml or less, and preferably 0.3 to 0.05 g/ml.

The polyamino acid particles prepared by the process of the present invention can be denatured by the following methods. For example, when the particles are obtained from an amino acid-NCA monomer such as an ester of N-carboxy anhydride of acidic amino acid, such as glutamic acid ester or aspartic acid ester, N-carboxy anhydride of basic amino acid, such as N-carbobenzoxylysine or N-carbobenzoxyornithine, or when the polymer particles are copolymers obtained by the copolymerization of one of these N-carboxylic acid anhydrides and an N-carboxy anhydride of a neutral amino acid, the surfaces of these particles can be made hydrophilic by hydrolyzing the particles on the surface to produce an amino group or carboxyl group on the surface. The surface of the particles can also be made hydrophilic by reacting polyamino acid particles with an alcohol amine such as ethanol amine, propanol amine, or butanol amine. In addition, polyamino acid particles are cross-linked by reacting with a diamine, such as ethylene diamine, propylene diamine, hexamethylene diamine, or octamethylene diamine, or a dicarboxylic acid, such as malonic acid, succinic acid, or adipic acid.

The polyamino acid particles prepared by the process of the present invention can be used as a coating material for papers, resins, rubbers, and fibers; particles for cosmetics; particles for diagnostic drugs; fillers for chromatography; and an encapsulating material for drugs, fertilizers, and perfumes.

For example, a sustained release drug can be produced by polymerizing N-carboxy anhydride in the presence of a physiologically active substance or by impregnating the resulting polyamino acid particles with a physiologically active substance.

Highly hydrophilic drugs with a small oil/water distribution rate and highly hydrophobic substances can be given as examples of suitable physiologically active substances. The physiologically active substances may be soluble in both oil and water and include anti-cancer drugs, antibiotics, physiologically active polypeptides, antifebriles, sedatives, immune activators, antiinflammatory agents, antitussive drugs, antiepileptic drugs, antihistamines, hypotensive diuretics, diabetes treatment agents, muscular relaxation agents, antitumor agents, antidepressants, antiallergic drugs, cardiac treatment agents, irregular pulse treatment agents, vasodilators, anticoagulants, antinarcotics, hemostatics, antituberculosis agents, and hormones.

Given as specific examples are anti-cancer drugs, such as adriamycin, mitomycin, bleomycin, cisplatin, fluorouracil, methotrexate, actinomycin D, Krestin, picibanil, and lentinan; polypeptides, such as insulin, somatostatin, corpus luteum hormone release hormone (LHRH), LHRH derivatives, prolactin, adrenocorticotrophic hormone, growth hormone, thyroid hormone release hormone, melanocyte trophic hormones, luteotropic-trophic hormone, paliprecin, calcitonin, oxytocin, accessory thyroid gland hormone, gastrin, tetragastrin hydrochloride, glucagon, pancreozymine, cholecystokinin, angiotensin, human placental lactogen, human fimbrio gonadotrophin, enkephalin, endorphin, kyotrophin, interferon, interleukin (I, II, III), tumor necrosis factor (TNF), tuftsin, thymopoietin, thymosin, thymostimulin, thymic humoral factor, circulating thymic factor, colony provocation factor, motiline, dinorphin, pompecin, neurotension, cerulein, pladeixin, urokinase, asparaginase, kallikrein, substance P, nerve growth factor, blood coagulation factor, lysozyme chloride, polymyxin B, colistin, gramicidin, and bacitracin; antibiotics, such as tetracyclines (chlortetracycline, oxytetracycline, doxycycline and tetracycline), penicillins, cephalosporins, streptomycin, novabioxin, neomycin, sulfonamides, erythromycin, colistin, lincomycin, nalidixic acid, apramycin, salinomycin, nigericin, kanamycin, kitasamycin, tylosin, furaltadone, pasocomycin, thiostrepton, gentamicin, tobramycin, spiramycin, ristocetin, soymycin, erythromycin, 5-o-mikaminotsurutailonolide, and dibekacin hydrochloride; antipyretics, such as sodium salicylate, sulpyrine, diclofenac sodium, indomethacin sodium, frephenamate sodium, pethidine hydrochloride, morphine hydrochloride, oxymorpholine, and tartaric acid lepophanol; sedatives, such as prochlorperazine, tricloperazine, chlorpromazine hydrochloride, atropine sulfate, and bromomethylscopolamine; antitussive expectorants, such as noscapine hydrochloride, codeine phosphate, methylephedrine hydrochloride, ephedrine hydrochloride, alloclamide hydrochloride, dihydrocodeine phosphate, chlophedianol hydrochloride, picoperidamine hydrochloride, chloperastine, isoproterenol hydrochloride, protokylol hydrochloride, salbutamol sulfate, and terbutaline sulfate; antidepressants, such as phenelzine sulfate, clomipramine, xyputyline, and imipramine; antiepileptics, such as ethosuximide, sodium acetazolamide, chlordiazepoxide hydrochloride, and sodium phenytoin; muscular relaxation agents, such as histidine hydrochloride and metoclopramide; antiallergic drugs, such as ketotifen fumarate, diphenhydramine hydrochloride, chlorpheniramine maleate, methdilazine hydrochloride, tripelennamine hydrochloride, clemizole hydrochloride, diphenylpyraline hydrochloride, and methoxyphenamine hydrochloride; hypotensive diuretics, such as clonidine hydrochloride, captopril, bunitrolol hydrochloride, hexamethonium, pramide, pentolinium, ecarazine hydrochloride, and mecamylamine hydrochloride; diabetes treatment agents such as glipizide, glymidine sodium, phenformin hydrochloride, metformin, and buformin hydrochloride; vasodilators, such as oxyfedrine hydrochloride, tolazoline hydrochloride, diltiazem hydrochloride, bamethan sulfate, and hexobendine; irregular pulse treatment agents, such as proplanolol hydrochloride, oxyprelol hydrochloride, bufetolol hydrochloride, and alprenolol hydrochloride; anticoagulants, such as sodium heparin and sodium citrate; hemostatics, such as acetomenaphthone, thrombin, thromboplastin, methydione sodium hydrogensulfite, tranexamic acid, i-aminocaproic acid, adrenochrom monoaminoguanidine metasulfonate, and sodium carbazochrom sulfonate; antinarcotic, such as levallorphan tartarate, naloxone hydrochloride, and nalorphine hydrochloride; antituberculosis agents, such as isoniazid, ethambutol and sodium para-aminosalicylate; and hormones, such as sodium dexamethasone sulfate, sodium phosphate prednisolone, prednisolone succinate, methimazole, sodium betamethazone phosphate, hexestrol phosphate, and hexestrol acetate.

In addition to physiologically active substances, additives commonly used in medicines such as, for example, solid diluents, carriers, binders, excipients, and other subsidiary agents, may be incorporated into the sustained release drugs. Specific examples of such other additives include tragacanth gum, acacia, corn starch, gelatin, alginic acid, magnesium stearate, algumin, aluminummonostearate, beeswax, saccharide, lactic acid, methyl paraben, propyl paraben, mannitol, propylene glycol, calcium silicate, silica, polyvinylpyrrolidone, setostearyl alcohol, polyoxyethylene sorbitanmonolaurate, ethyl lactate, sorbitantrinarate, ethyl laurate, calcium stearate, talc, oleic acid, and linolic acid.

The content of the above-mentioned physiologically active substances is in the range of 0.01 to 60% (v/v), preferably 0.1 to 50% (v/v), of the amount of the polyamino acid particles, although the content is varied depending on the types of physiological active substance, the intended pharmacological effect, the target sustained release time, and the like.

These sustained release drugs may be used in any optional form, such as a peroral drug, a percutaneous drug, a suppository, a pernasal drug, an oral cavity administration drug, or a perintraocular drug.

Moreover, it is possible to provide an ultraviolet preventive effect to the polyamino acid particles by adding a UV preventive agent instead of the physiologically active substances.

Both organic and inorganic UV preventive agents can be used. Given as examples of the organic UV preventive agents are amino benzoate UV preventives, such as 2-ethylhexyl-p-dimethylaminobenzoate, amino-p-dimethylaminobenzoate, glyceryl-p-aminobenzoate, ethyl-p-diethylaminobenzoate, ethyl-p-diethylaminobenzoate, and glyceryl-mono-p-aminobenzoate; salicylate UV preventives, such as p-tert-butyl salicylate, p-octylphenyl salicylate, and dipropylene glycol salicylate; benzophenone UV preventives such as 2-hydroxy-4-methoxybenzophenone; benzotriazole UV preventives such as 2-(2'-hydroxy-5-methylphenyl)benzotriazole; cinnamate UV preventives; such as 2-ethoxyethyl-p-methoxycinnamate, 2,2'-bis-(p-methoxystyryl)-ethyl-p-methoxycinnamate, 2-ethoxyethyl-p-methoxycinnamate, and methyl-2,5-diisopropyl cinnamate; uroxanic acid UV preventives, such as uroxanic acid and ethyl uroxanate; vitamin UV preventives, such as vitamin A1, vitamin A2, vitamin A3, vitamin B2, and vitamin B12; nickel chelate UV preventives, hindered amine UV preventives, 4-tert-butyl-4'-methoxydibenzoylmethane, octyl p-dimethyl-aminobenzoate, and glyceryl di-p-methoxy cinnamate mono-2-ethylhexanoate.

Among these UV preventives, particularly preferred are 4-tert-butyl-4'-methoxy-dibenzoylmethane, octyl p-dimethyl-aminobenzoate, glyceryl di-p-methoxy cinnamate mono-2-ethylhexanoate, 2-hydroxy-4-methoxybenzophenone, and 2-(2'-hydroxy-5-methylphenyl)benzotriaole.

Of these compounds, 4-tert-butyl-4'-methoxydibenzoylmethane has a high capacity for absorbing ultraviolet rays of the A-wavelength region of 320 to 400 nm, octyl p-dimethylaminobenzoate, glyceryl di-p-methoxy cinnamate mono-2-ethylhexanoate, and 2-hydroxy-4-methoxybenzophenone have a high capacity for absorbing ultraviolet rays of the B-wavelength region of 280 to 320 nm and, 2-(2'-hydroxy-5-methylphenyl)benzotriaole has a high capacity for absorbing ultraviolet rays of both the A-wavelength region and the B-wavelength region.

Inorganic UV preventives are typified by metal oxides such as titanium oxide, zinc oxide, and iron oxide. Titanium oxide and zinc oxide are particularly preferred inorganic UV preventives.

These UV preventives may be used either individually or in combination of two or more.

Other features of the invention will become apparent in the course of the following description of the exemplary embodiments which are given for illustration of the invention and are not intended to be limiting thereof.

EXAMPLES

In the Examples below, the average particle size of polymer particles was measured by observing these polymer particles using transmission type microscopy; the CV number of polymer particles was calculated according to the following formula, $$CV \text{ Number } (\%) = \left(\frac{\text{Standard deviation of the average particle size}}{\text{The average particle size}}\right) \times 100;$$

the limiting viscosity of polymers was measured in dichloroacetic acid at 30° C.; and the molecular weight of poly-γ-benzyl-L-glutamate was measured by the following formula (1) and that of poly-γ-methyl-L-glutamate, by the following formula (2), $$[\eta] = 2.78 \times 10^{-5} \times M^{0.87} \tag{1}$$

$$[\eta] = 2.90 \times 10^{-4} \times M^{0.74} \tag{2}$$

wherein $[\eta]$ is the limiting viscosity and M is the molecular weight.

Example 1

10 ml of dry diethyl ether, 1 g of glutamic acid-γ-methyl ester-NCA (hereinafter abbreviated to MLG-NCA), and 0.1 mmol of triethylamine were added to a dry 50 ml flask. The mixture was polymerized while stirring at room temperature for 5 hours to produce polyamino acid particles. After polymerization, the polymer was poured into 100 ml of methanol, filtered, and dried to obtain dry polymer (PMLG) to be subjected to analysis. The yield of the polymer was 92%. The limiting viscosity of the polymer measured in dichloroacetic acid was 1.42 and the molecular weight was 97,000. The polymer particles had an average particle diameter of 53 μm and a CV value of 48%. The particles were porous and had a bulk specific gravity of 0.27 g/ml.

Example 2

Polyamino acid particles were prepared in the same manner as in Example 1, except that L-glutamic acid-γ-benzyl ester-NCA was used instead of MLG-NCA. The yield of poly-γ-benzyl-L-glutamate was 100%. The limiting viscosity of the polymer was 0.94 and the molecular weight was 160,000. The polymer particles had an average particle diameter of 72 μm and a CV value of 51%. The particles were porous and had a bulk specific gravity of 0.25 g/ml.

Example 3

Polyamino acid particles were prepared in the same manner as in Example 1, except that L-glutamic acid-γ-ethyl ester-NCA was used instead of MLG-NCA. The yield of poly-γ-ethyl-L-glutamate was 100%. The limiting viscosity of the polymer was 1.12 and the molecular weight was70,000. The polymer particles had an average particle diameter of 58 μm and a CV value of 52%. The particles were porous and had a bulk specific gravity of 0.26 g/ml.

Example 4

1 g of MLG-NCA and 0.1 mmol of n-butylamine were added to 10 ml of diisopropyl ether, and the mixture was stirred at room temperature for 5 hours to polymerize. After polymerization, the polymer was poured into 100 ml of methanol, filtered, and dried to obtain PMLG particles. The yield of PMLG was 98%. The limiting viscosity of the polymer was 0.84 and the molecular weight was 48,000. The polymer particles had an average particle diameter of 13 μm and a CV value of 22%. The particles were porous and had a bulk specific gravity of 0.3 g/ml.

Example 5

PMLG particles were prepared in the same manner as in Example 4, except that cyclohexane was used instead of diisopropyl ether. The yield of PMLG was 100%. The limiting viscosity of the polymer was 0.76 and the molecular weight was 41,000. The polymer particles had an average particle diameter of 11 μm and a CV value of 19%. The particles were porous and had a bulk specific gravity of 0.28 g/ml.

Example 6

Poly-γ-benzyl-L-glutamate (PBLG) was prepared in the same manner as in Example 4, except that cyclohexane was used instead of diisopropyl ether and γ-benzyl-L-glutamate-N-carboxy anhydride (BLG-NCA) was used instead of MLG-NCA. The yield of PBLG was 100%. The limiting viscosity was 0.60 and the molecular weight was 97,000. Half the amount of the polymer was freeze-dried to obtain PBLG particles. The PBLG particles had an average particle diameter of 33 μm and a CV value of 41%. The particles were porous and had a bulk specific gravity of 0.31 g/ml.

Example 7

PBLG was prepared in the same manner as in Example 6, except that n-butylamine was used instead of triethylamine. After polymerization, half the product was poured into methanol. Precipitated PBLG was filtered and dried. The yield of PBLG was 98%. The limiting viscosity of the polymer was 0.35 and the molecular weight was 51,000. The remaining half the polymer was freeze-dried to obtain PBLG particles. The PBLG particles had an average particle diameter of 14 μm and a CV value of 27%. The particles were porous and had a bulk specific gravity of 0.33 g/ml.

Polyamino acid particles having a high molecular weight and a small bulk specific gravity can be manufactured very easily without requiring specific procedures from amino acid-NCA using the specific solvent with excellent reproducibility by means of the process of the present invention.

Obviously, numerous modifications and variations of the present invention are possible in light of the above teachings. It is therefore to be understood that, within the scope of the appended claims, the invention may be practiced otherwise than as specifically described herein.

We claim:

1. A process for preparing poly-α-amino acid particles comprising polymerizing an α-amino acid-N-carboxy anhydride using a polymerization initiator in an organic solvent having a water content of 2 wt % or less in which both the solubility of the α-amino acid-N-carboxy anhydride and the solubility of the produced poly-α-amino acid are at most 0.1 g/100 ml at 25° C. said organic solvent being present in an amount of 1 to 50 wt % based on said α-amino acid-N-carboxy anhydride.

2. The process for preparing poly-α-amino acid particles according to claim 1, wherein the solubility of the α-amino acid-N-carboxy anhydride and the solubility of produced poly-α-amino acid in said organic solvent are both at most 0.05 g/100 ml at 25° C.

3. The process for preparing poly-α-amino acid particles according to claim 1, wherein said organic solvent is at least one organic solvent selected from the group consisting of aliphatic hydrocarbons having 5–20 carbon atoms, aromatic hydrocarbons having 6–9 carbon atoms, and ethers having 4–20 carbon atoms.

4. The process for preparing poly-α-amino acid particles according to claim 1, wherein the α-amino acid-N-carboxy anhydride is used in the amount of 1 to 50 wt % of the organic solvent.

5. The process for preparing poly-α-amino acid particles according to claim 1, wherein the polymerization initiator is used in the amount of 0.0002 to 0.5 mol for one mol of the α-amino acid-N-carboxy anhydride.

6. The process for preparing poly-α-amino acid particles according to claim 1, wherein the poly-α-amino acid particles are porous materials.

7. The process for preparing poly-α-amino acid particles according to claim 1, wherein the poly-α-amino acid particles have a bulk specific gravity of 0.35 g/ml or less.

* * * * *

UNITED STATES PATENT AND TRADEMARK OFFICE
CERTIFICATE OF CORRECTION

PATENT NO. : 5,854,384
DATED : December 29, 1998
INVENTOR(S) : Kyoko KURODA et al.

It is certified that error appears in the above-identified patent and that said Letters Patent is hereby corrected as shown below:

On the title page, item [73] the Assignee should be:

-- [73] Assignee: JSR Corporation, Tokyo, Japan--

Signed and Sealed this

First Day of June, 1999

Attest:

Q. TODD DICKINSON

*Attesting Officer*     *Acting Commissioner of Patents and Trademarks*